US012734273B2

(12) United States Patent
Adam

(10) Patent No.: US 12,734,273 B2
(45) Date of Patent: Sep. 15, 2026

(54) METHODS TO INHIBIT OSTEOPOROSIS THROUGH IMPLANTATION

(71) Applicant: Tarifa Adam, Albany, NY (US)

(72) Inventor: Tarifa Adam, Albany, NY (US)

( * ) Notice: Subject to any disclaimer, the term of this patent is extended or adjusted under 35 U.S.C. 154(b) by 412 days.

(21) Appl. No.: 18/493,531

(22) Filed: Oct. 24, 2023

(65) Prior Publication Data

US 2025/0127959 A1 Apr. 24, 2025

(51) Int. Cl.
*A61L 27/30* (2006.01)
*A61L 27/02* (2006.01)
*A61L 27/54* (2006.01)

(52) U.S. Cl.
CPC ........... *A61L 27/306* (2013.01); *A61L 27/025* (2013.01); *A61L 27/54* (2013.01); *A61L 2300/10* (2013.01); *A61L 2300/412* (2013.01); *A61L 2430/02* (2013.01)

(58) Field of Classification Search
CPC ...... A61L 27/306; A61L 27/025; A61L 27/54; A61L 2300/10; A61L 2300/412; A61L 2430/02
See application file for complete search history.

(56) References Cited

U.S. PATENT DOCUMENTS

2014/0302109 A1* 10/2014 Webster .................. A61L 27/22
514/16.7

* cited by examiner

*Primary Examiner* — Andrew Restaino

(57) ABSTRACT

In an example, nitrogen is implanted into a bone and heated so as to be incorporated into the bone.

12 Claims, 1 Drawing Sheet

110

Nitrogen

210

METHODS TO INHIBIT OSTEOPOROSIS THROUGH IMPLANTATION

TECHNICAL FIELD

The present invention relates generally to prevention of osteoporosis, and, in particular embodiments, to methods to inhibit osteoporosis through implantation.

BACKGROUND

Poor bone density has been one of the primary reasons for the onset of osteoporosis. Therefore, any treatment to improve the density of the bone can help retard or arrest the onset of osteoporosis.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

Figures 1, 2, 3:
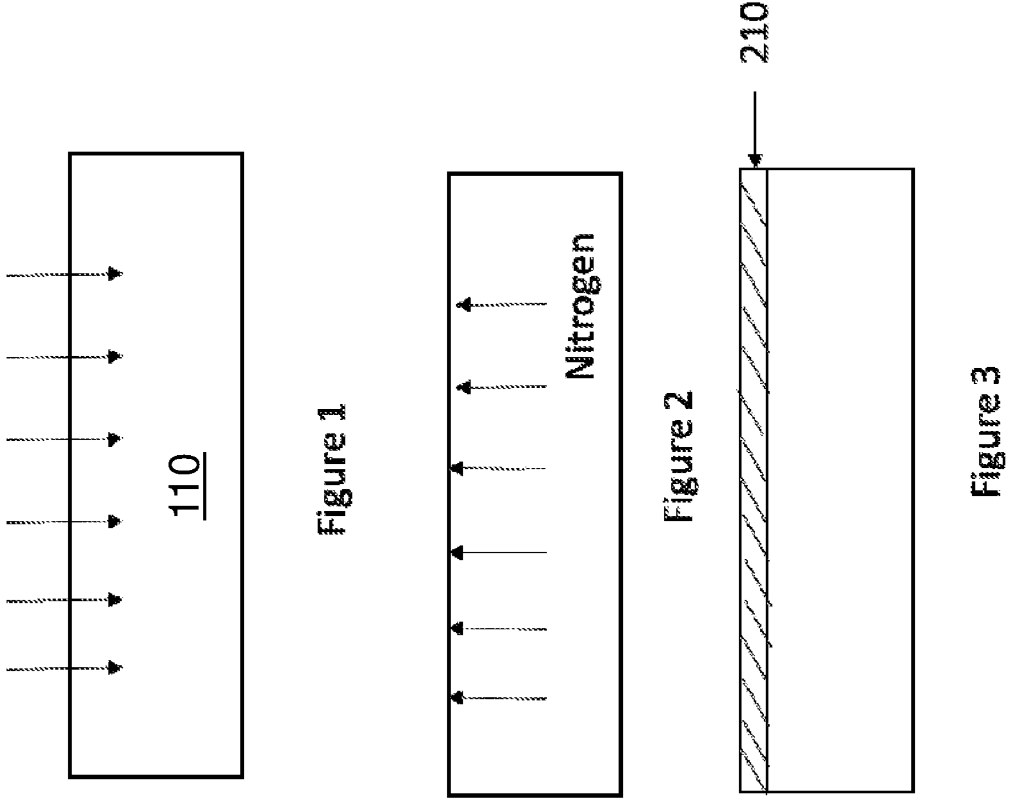
FIG. 1 illustrates a process of implanting nitrogen into a bone structure in accordance with embodiments of the invention.
FIG. 2 illustrates performing a heat treatment to the nitrogen implanted bone in accordance with embodiments of the invention.
FIG. 3 illustrates a bone structure after heat treatment in accordance with embodiments of the invention.

The present disclosure relates to the field of biomedical implantation and a method for practicing the same. More particularly, the present disclosure relates to a bone whose structure has been modified in order to improve the strength and therefore prevent the progression of osteoporosis.

One possible approach for creating stronger bones is through the implantation of nitrogen and subsequent heat treatment where the nitrogen diffuses towards the surface of the bone. Nitrogen at the surface helps improve the strength of the bone by filling dangling bonds at the bone interface and thereby improving the bone strength. Improved bone strength then helps retard or arrest the onset of osteoporosis in living beings.

Turning to the drawings, FIG. 1 shows a pictorial representation of nitrogen being implanted into the bone 110. Bone 110 may be in any region of the body of a living being and of any shape or size. Nitrogen is then implanted in to the top of the bone 110.

Any method of implantation can be used. While it is preferred nitrogen to be selectively implanted into the target bone through the use of masking techniques, it is not a requirement for this method. The recommended dose can be in the range of up to $1\times10^{15}/cm^2$.

In FIG. 2, heat is applied in the range of up to 50° C. and the implanted nitrogen is then brought to the surface of the bone (110) through diffusion. Any process of heat treatment will suffice.

FIG. 3 depicts the structure of the bone subsequent to the method described in the schematic of FIG. 2. After the diffusion of nitrogen towards the surface, the layer 210 is formed. The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses.

Accordingly, the description is not intended to limit it to the form disclosed herein. Also, it is intended that the appended claims be construed to include alternative embodiments.

What is claimed is:

1. A method comprising:
implanting nitrogen into a bone; and
heating the bone with the implanted nitrogen.

2. The method of claim 1, wherein the implantation is performed in a dose range up to $1\times10^{15}/cm^2$.

3. The method of claim 1, wherein the heating is performed in a temperature range of up to 50° C.

4. The method of claim 1, wherein the step of implanting the nitrogen comprises selectively implanting nitrogen into a portion of the bone.

5. The method of claim 4, wherein the portion of the bone is a periosteum.

6. A method comprising:
implanting nitrogen into a bone having an inner core and a peripheral region; and
heating the bone with the implanted nitrogen such that nitrogen is incorporated into the peripheral region of the bone.

7. The method of claim 6, wherein heating the bone comprises diffusing the implanted nitrogen from an implanted region of the bone toward a surface of the peripheral region.

8. The method of claim 6, wherein the implantation is performed in a dose range up to $1\times10^{15}/cm^2$.

9. The method of claim 6, wherein the heating is performed in a temperature range of up to 50° C.

10. The method of claim 6, wherein the peripheral region of the bone is a periosteum.

11. A method of modifying a bone structure, the method comprising:
providing a bone having an inner core and a peripheral region, the peripheral region including a periosteum;
selectively implanting nitrogen into a target portion of the bone through use of a masking technique, wherein the target portion includes the periosteum, and wherein the implanting is performed at a dose in a range of up to $1\times10^{15}/cm^2$; and
heating the bone with the implanted nitrogen at a temperature in a range of up to 50° C., such that at least a portion of the implanted nitrogen diffuses from an implanted region toward a surface of the bone and is incorporated into the peripheral region of the bone to form a nitrogen-containing layer at the surface of the bone, wherein the nitrogen-containing layer fills dangling bonds at a bone interface to improve a strength of the bone.

12. The method of claim 11, wherein the target portion of the bone is the periosteum.

* * * * *